United States Patent [19]

Agdanowski et al.

[11] Patent Number: 4,648,398
[45] Date of Patent: Mar. 10, 1987

[54] NASAL CANNULA

[75] Inventors: Ronald T. Agdanowski, St. Peters; James A. Geil, St. John; Bernard J. Tatro, Manchester, all of Mo.

[73] Assignee: Sherwood Medical Company, St. Louis, Mo.

[21] Appl. No.: 666,847

[22] Filed: Oct. 31, 1984

[51] Int. Cl.$^4$ ............................................. A61U 15/08
[52] U.S. Cl. ............................................... 128/207.18
[58] Field of Search ...................... 128/207.18, 203.22, 128/152

[56] References Cited

U.S. PATENT DOCUMENTS

| Re. 29,487 | 12/1977 | Gardner, Jr. | 128/152 |
| 718,785 | 1/1903 | McNary | |
| 2,735,432 | 2/1956 | Hudson | 128/348 |
| 2,931,358 | 4/1960 | Sheridan | 128/207.18 |
| 3,726,275 | 4/1973 | Jackson et al. | 128/206 |
| 3,915,173 | 10/1975 | Brekke | 128/351 |
| 3,993,081 | 11/1976 | Cusseil | 128/351 |
| 4,156,426 | 5/1979 | Gold | 128/205 |
| 4,367,735 | 1/1983 | Dali | 128/207.18 |

Primary Examiner—Henry J. Recla
Attorney, Agent, or Firm—Stanley N. Garber; Andrew J. Beck; William R. O'Meara

[57] ABSTRACT

A nasal cannula is provided that includes a pair of sponge-like nasal tips for insertion into the nostrils of a patient and which are easily, manually compressible to reduce the size of the tips for easy insertion and which have a relatively slow rate of expansion.

1 Claim, 7 Drawing Figures

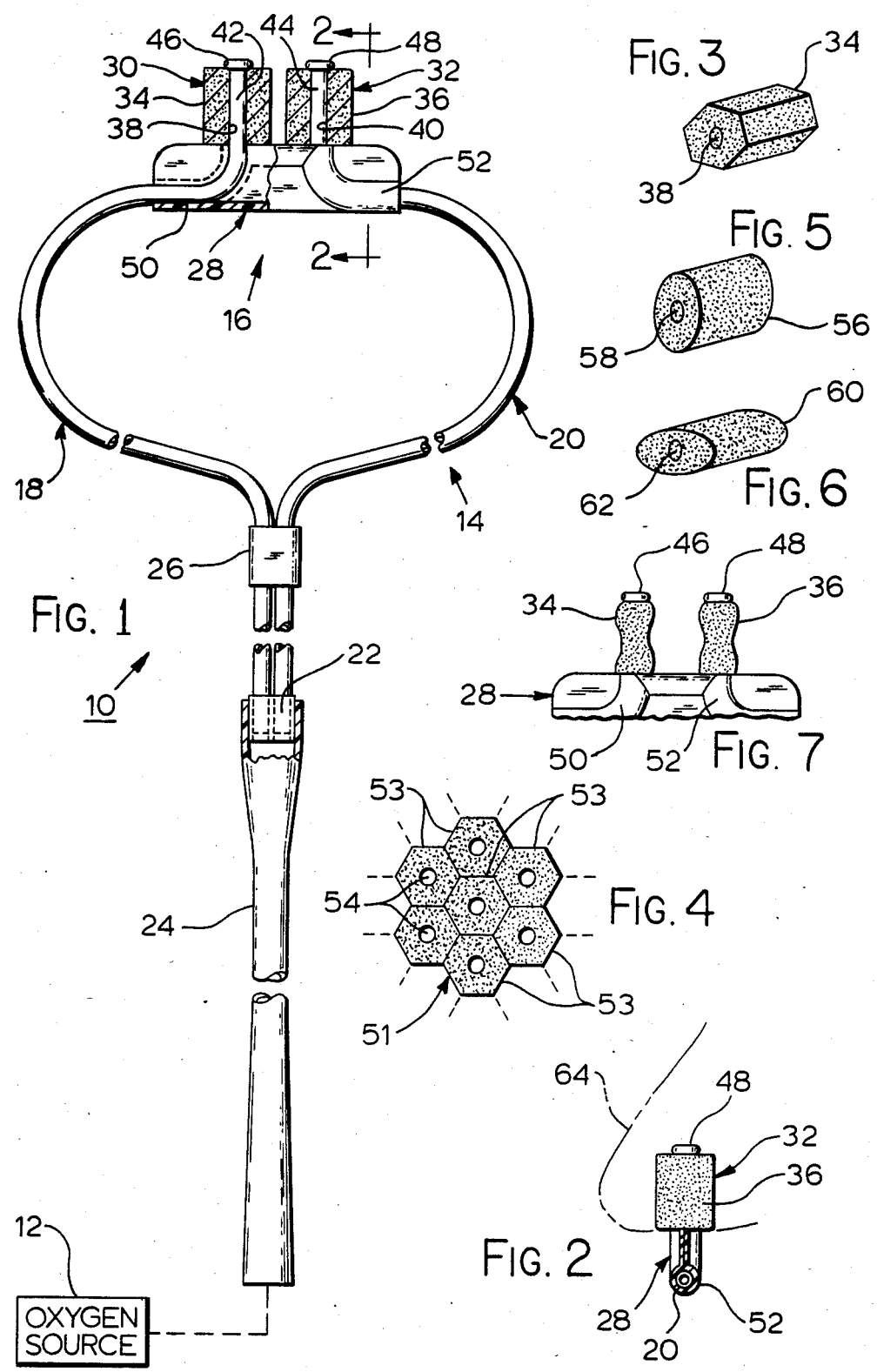

NASAL CANNULA

DESCRIPTION

Technical Field

This invention relates to nasal cannulas used in the administration of gases to patients, and more particularly to a nasal cannula having nostril seals.

Background Art

Nasal cannulas are used to administer gases, such as anesthetic gases or breathing gases, such as oxygen or air, to patients. Nasal cannulas generally include a pair of nasal cannula tips having gas flow passages therethrough and which are adapted to be inserted into the nostrils of the patient and connected to a source of gas. It is often desirable or necessary to provide a seal between the outer surface of the cannula tip and the nostril to prevent gas leaking into the atmosphere or ambient air flowing into the nostrils of the patient. Since nasal cannulas are often maintained in the patient for a considerable length of time, it is especially important to provide a nasal cannula that provides a good seal, does not cause excessive discomfort to the patient and minimizes irritation to the nostrils of the patient.

Various types of nasal cannulas have been proposed. Some have proposed applying soft rubber tips adapted to be inserted into and to seal the nostrils but these have been subject to bending which may close off the gas flow passage through the tip especially during movement of the patient. Some have proposed sponge or foam pads or tips for insertion into the nostrils but such tips had to be large enough to seal and were therefore difficult to insert and remove without irritation of the nostrils and discomfort to the patient. Both rubber and sponge tips were somewhat difficult to insert into the nostrils and, in many cases, difficult to remove so that insertion and removal often produced discomfort to the patient.

SUMMARY OF THE INVENTION

It is therefore an object of the present invention to provide an improved nasal cannula that substantially obviates or reduces one or more of the above mentioned problems.

it is another object of the present invention to provide a nasal cannula that is especially easily inserted into the nostrils of a patient and with minimal discomfort and which provides good nostril seals.

Still another object is to provide a nasal cannula of the above type which provides a good seal with minimal discomfort and which greatly resists bending and closure of the gas-flow passage therethrough due to patient movement.

Still another object is to provide an improved nasal cannula and method of inserting the same into the nostrils of a person.

In accordance with one aspect of the present invention, a nasal cannula is provided which includes a pair of nasal tips adapted for respective insertion into the nostrils of a patient, each of the tips includes a seal having a flow passage therethrough and which is formed of a resilient, compressible foam material having a rate of recovery from 60% compression thereof to 40% compression thereof in from 1 to 60 seconds, the seals having a size and shape adapted to be manually compressed and respectively insertable into the nostrils of the patient and expandable thereafter to obturate the nostrils.

These, as well as other objects and advantages of the present invention, will become apparent from the following detail description and accompanying drawing.

BRIEF DESCRIPTION OF THE DRAWING

FIG. 1 is an elevational view, partly in section, of a nasal harness including a nasal cannula in accordance with a preferred embodiment of the present invention;

FIG. 2 is a cross-sectional view taken along a line 2—2 of FIG. 1 and with the nasal cannula inserted into a nose shown in phantom;

FIG. 3 is a perspective view of a seal member of FIG. 1;

FIG. 4 shows one method of punching narine seal members from stock material;

FIG. 5 is a perspective view of a seal member of modified shape;

FIG. 6 is perspective view of a seal member of another modified shape; and

FIG. 7 is a fragmentary elevational view of a portion of the nasal cannula of FIG. 1 after the nasal seal members have been manually reduced in size preparatory to insertion into the nose of a patient.

DETAILED DESCRIPTION OF THE PREFERRED EMBODIMENTS

Referring now to the drawing and particularly to FIG. 1, a nasal harness assembly indicated generally at 10 is shown connected to a source of gas such as an oxygen source 12. The assembly 10 includes a nasal harness 14 including a nasal cannula 16 connected by gas supply tubes 18 and 20 to a connector 22. Connector 22 is sealingly connected to one end of a main gas supply tube 24 to connect the supply tubes 18 and 20 and nasal cannula 16 with the oxygen source 12. A conventional slip ring 26 encircles the two supply tubes 18 and 20 so that these tubes may be adjusted for proper fitting after the harness 14 is applied to a patient. The tubes 18 and 20 may be placed around the ears to provide additional support for the harness where possible and desirable.

The nasal cannula 16 is shown for illustration as including a bridge member 28 carrying a pair of gas outlets or nasal tips 30 and 32 in spaced relation for insertion in the nostrils of a patient.

The nasal tips 30 and 32, respectively, include soft, compressible, resilient, foam or sponge-like seals 34 and 36 having passages 38 and 40, respectively, which extend through the seals. Nasal tips 30 and 32 in the illustrated embodiment, also include air-flow tubes or conduits 42 and 44, respectively, which extend longitudinally through the seal passages 38 and 40, respectively. The distal ends of conduits 42 and 44 are provided with integral annular flanges 46 and 48, respectively. The conduits 42 and 44 are connected in fluid communication with the gas supply tubes 18 and 20, respectively, and are preferably integral distal end portions of the supply tubes 18 and 20 as shown in FIG. 1.

Bridge 28, also shown in FIG. 2, is illustrated in the form of an unitary or single-piece, molded plastic sheet member which when folded upon itself provides a pair of channels 50 and 52 through which the distal end portions of the supply tubes 18 and 20 pass. The engaging facing sides of the bridge member 28 may be secured together by any suitable means, for example, heat welding or by an adhesive. U.S. application, Ser. No.

596,754, filed Apr. 4, 1984, and which is assigned to the same assignee as this application, discloses a nasal harness having a bridge similar to bridge 28. The nasal seals 30 and 32 are disposed in tight sealing engagement with the outer surfaces of the conduits 42 and 44. Seal 30 is located in position on conduit 42 between flange 46, which has a greater outer diameter than that of passage 38, and the upper edge of the bridge 28. Similarly, seal 36 is disposed between a similar flange 48 on conduit or tube 44 and the upper edge of bridge 28.

The seals 34 and 36 are elongate members sized to close nostrils against the flow of air or gas into or out of the nostrils except through the passages 38 and 40 or conduits 42 and 44 where used and after the seals are expanded into contact with the walls of the nostrils. While the seals 34 and 36 may be of various shapes, as will be further discussed herein, they are shown hexogonal, as is apparent from FIG. 3, i.e., hexagonal in cross-section. By making the seals 34 and 36 hexagonal in cross-section, the seals can be punched from sheet material with minimal waste. For purpose of illustration, a sheet 51 is shown in FIG. 4 cut into a plurality of contiguous nasal seals indicated at 53 that are identical in shape to seals 34 and 36 of FIG. 1. The sheet 51 may, for example, be cut by a die or dies having shapes complementary to the seals shown and which will provide each with a hole 54. It is seen that there is no waste material between adjacent seals 53. Other shapes of course, such as rectangular, square, and others may also be punched from sheet material with little waste.

Where desired, the nasal seals may be made in a variety of other shapes. For example, in FIG. 5, a sponge-like seal 56 having an opening 58 extending through it is in the form of an elongated cylinder circular in cross-section. In FIG. 6, a sponge-like seal 60 is shown in the form of a sponge-like elongated member having an opening 62 and which is generally elliptcal in cross-section. While these seals will generally produce some waste material if they are punched from sheet material in a manner similar to that shown in FIG. 4, such are nevertheless suitable for use in place of the seals 34 and 36 of FIG. 1.

The soft sponge-like material from which the nasal seals 34 and 36 or the seals 56 and 60 are made, is a foam material that is readily compressed and then, when the forces are removed, slowly returns to its unrestricted configuration when free to do so or to a shape determined by the shape of the nostril in which it may be disposed. The material expands at a predetermined rate from the compressed state to provide a sufficient time delay or recovery time to enable the nasal tips 30 and 32 to be readily inserted into the nostrils of a patient while the seals are reduced in diameter and smaller than the nostrils. The seals then expand outwardly against the walls of the nostrils with some pressure applied to the nostrils due to the resiliency of the material to thereby provide good nasal seals. Depending upon the particular construction of the nasal cannula or bridge, one of the seals 34 or 36 may be compressed and inserted into one nostril and then the other seal may be compressed and inserted into the other nostril. On the other hand, both seals can be compressed and substantially simultaneouly inserted into the nostrils.

FIG. 7 illustrates the seals 34 and 36 when manually compressed by pinching between the fingers, such as the thumb and index finger. This may be done, for example, by pinching and twirling each back and forth until both seals 34 and 36 have relatively small outer diameters. When in the compressed shape indicated in FIG. 7, the nasal tips are substantially smaller than the nostrils and are easily inserted into the nostrils of the patient without the necessity of forcing them into the nostrils and without nasal irritation. The seals expand and close the nasal passages, such as indicated in FIG. 2 where a nose is shown in phantom at 64.

Some such materials that are usable in making nasal cannulas in accordance with present invention are compositions composed of relatively soft foam materials having such characteristics as a rate of recovery from 60% compression to 40% compression in a period of time from about 1 to about 60 seconds, and an equilibrium pressure at 40% compression of from about 0.2 to 1.3 p.s.i. as will be discussed hereafter. The average outer diameter each of the seals is preferably about $\frac{5}{8}$ inch or 1.59 cm, the length is preferably about $\frac{1}{2}$ inch or 1.27 cm, and with the through opening having a diameter preferably about $\frac{1}{8}$ inch or 0.32 cm. These dimensions are suitable for most adults. The average outer diameter and length dimensions, however, may vary from about $\frac{1}{4}$ inch (0.635 cm) to 1 inch (2.54 cm).

Specific materials useful in making seals 34 and 36 in accordance with the present invention may be made from a variety of sponge-like or foam materials, such as polymeric materials, that provide the above mentioned desirable characteristics. For example, useful polymeric foam materials and methods of making them are hereby incorporated herein by reference to U.S. Pat. No. Re 29 487, reissued Dec. 6, 1977.

The manner in which the recovery rate or time delay of the foamed polymer may be determined is by use of a parallel plate guage and by compressing the seal so that the diameter is about 40% of its uncompressed original diameter and then allowing the seal to increase in diameter until it corresponds to about 60% reduction of its original diameter. As previously mentioned, this delay time or rate of recovery may be between 1 and 60 seconds, and preferably between about 2 and 30 seconds. The most preferred delay time is at least 4 seconds and less than about 20 seconds. This latter range provides seals which are substantially ideal for a nasal cannula.

The previously mentioned 40% compression equilibrium pressure testing of the polymeric foam may be accomplished by employing an Instron Universal testing instrument Model TTC having a parallel plate specimen holder and measured when 40% of the compression is present as described in the above-mentioned referenced patent. At this point the p.s.i. rating is preferably between 0.2 and 1.3 p.s.i.

Good results are obtainable by employing seals made from polyvinyl chloride based polymers of the type disclosed in the examples in the above referenced patent. The recovery rate of a resilient plasticized foam of this type may be varied by selection of the components of the foam and relative amounts thereof. Some foam materials from which the seals 34 and 36 may be made can be purchased from the E.A.R. Division of the Cabot Corporation, Indianapolis, Ind., the materials being known as C-3001 and C-3002. In addition to the materials mentioned in the above referenced patent, a polyurethane foam seal material having characteristics similar to those previously mentioned herein are also usable. A polyurethane foam material having characteristics of the above-described type and ranges may be obtained from the Specialty Composites Corporation of Newark, Del.

Nasal harnesses in accordance with the present invention are very simple to use and effective to seal the nostrils. The seals 34 and 36 are soft and easily compressed to reduce their outer diameters for easy insertion into the nostrils without irritating the walls of the nostrils. Because of the relatively long expansion delay time or recovery rate, both seals (or one at a time) can be compressed by the fingers and inserted into the nostrils without hurrying the insertion. After insertion, the seals expand within a desirable length of time to obturate the nostrils about the conduits 42 and 44, i.e., gas can flow into or out of the nostril only through the passages or conduits of the tips 30 and 32. The pressure exerted at about 40% compression being between about 0.2 and 1.3 p.s.i. so as to provide a good seal without undesirably high pressures and therefore little discomfort to the patient. The expansion force of the nasal tip seals 34 and 36 when expanded within the nostrils not only seals the nostrils about the conduits 42 and 44 but also serves to affix or hold the tips 30 and 32 in place within the nostrils during normal movement of the patient. The conduits 42 and 44 and supply tubes 18 and 20 may be formed of a suitable plastic such as polyvinyl chloride. The conduits may therefore be made relatively stiff so that the conduits support the seals and resist inadvertent bending and occlusion of the nasal tips. The connector 22, main supply tube 24, slip ring 26, and bridge 28 may be made of a suitable plastic such as polyvinyl chloride.

As changes could be made in the above described construction and method without departing from the true spirit and scope of the invention, it is intended that all matter contained in the above description and shown in the accompanying drawings be interpreted as illustrative.

What is claimed is:

1. A nasal cannula comprising a pair of nasal tips, a bridge connecting said tips together for respective insertion into the nostrils of a patient, each of said tips including a resilient, compressible foam seal, and gas flow passage means extending therethrough for connection with a source of gas, each of said foam seals having a rate of recovery from 60% compression thereof to 40% compression thereof in a time range between about 1 and 60 seconds, said seals having a size adapted to be manually compressed and respectively insertable into the nostrils of the patient and expandable thereafter to obturate the nostrils about said passage means, said passage means including a pair of conduits respectively extending through said seals and connectable to a source of gas, said pair of conduits respectively including a pair of gas supply tubes extending through said bridge, each of said conduits including an annular radial flange at the distal end thereof, and each of said seals is disposed between the flange of its respective conduit and said bridge.

* * * * *